United States Patent
Zilberstien et al.

(10) Patent No.: US 11,457,884 B2
(45) Date of Patent: *Oct. 4, 2022

(54) MOVING PARTS IN A NUCLEAR MEDICINE (N-M) IMAGING SYSTEM

(71) Applicant: Spectrum Dynamics Medical Limited, Road Town (VG)

(72) Inventors: Yoel Zilberstien, Herzlia (IL); Nathaniel Roth, Tel-Aviv (IL); Idan Fogel, Netanya (IL); Baha Eldeen Kassem, Mukaibla (IL); Sajed Haj-Yahya, Taybe (IL)

(73) Assignee: Spectrum Dynamics Medical Limited, Road Town (VG)

( * ) Notice: Subject to any disclaimer, the term of this patent is extended or adjusted under 35 U.S.C. 154(b) by 0 days.

This patent is subject to a terminal disclaimer.

(21) Appl. No.: 17/120,394

(22) Filed: Dec. 14, 2020

(65) Prior Publication Data
US 2021/0093270 A1   Apr. 1, 2021

Related U.S. Application Data

(63) Continuation of application No. 16/756,492, filed as application No. PCT/IB2018/058097 on Oct. 18, 2018, now Pat. No. 10,863,956.
(Continued)

(51) Int. Cl.
*A61B 6/00* (2006.01)
*A61B 6/03* (2006.01)

(52) U.S. Cl.
CPC ............ *A61B 6/4476* (2013.01); *A61B 6/037* (2013.01)

(58) Field of Classification Search
CPC .............................. A61B 6/4476; A61B 6/037
See application file for complete search history.

(56) References Cited

U.S. PATENT DOCUMENTS

| | | |
|---|---|---|
| 3,902,070 A | 8/1975 | Amor, Jr. et al. |
| 4,057,726 A | 11/1977 | Jaszczak |

(Continued)

FOREIGN PATENT DOCUMENTS

| | | |
|---|---|---|
| EP | 0283870 B1 * | 10/1990 |
| WO | WO 2013/168111 | 11/2013 |

(Continued)

OTHER PUBLICATIONS

Official Action dated Jun. 10, 2021 From the US Patent and Trademark Office Re. U.S. Appl. No. 16/756,511. (31 Pages).
(Continued)

*Primary Examiner* — Marcus H Taningco

(57) ABSTRACT

A Nuclear Medicine (N-M) imaging system including a gantry having a stationary stator and a rotor rotatably mounted on the stator and including detection units. The rotor is driven by a rotor driving assembly including a linear encoder. The detection units mounted on the rotor include scanning columns having one or more Multi-Pixel Photon Counter (MPC) mounted on one or more extendable arm. The gantry also includes flat cables connecting the controller with gantry components, e.g., the scanning column Multi-Pixel Photon Counters (MPC). The scanning columns are pivotably moveable by a scanning column driver system including a rotary encoder.

26 Claims, 8 Drawing Sheets

Related U.S. Application Data

(60) Provisional application No. 62/574,277, filed on Oct. 19, 2017.

(56) References Cited

U.S. PATENT DOCUMENTS

| | | | |
|---|---|---|---|
| 4,209,700 A | 6/1980 | Stoddart | |
| 6,140,650 A | 10/2000 | Berlad | |
| 6,188,743 B1* | 2/2001 | Tybinkowski | A61B 6/035 |
| | | | 378/4 |
| 6,212,251 B1 | 4/2001 | Tomura et al. | |
| 6,242,743 B1 | 6/2001 | DeVito et al. | |
| 7,592,597 B2 | 9/2009 | Hefetz et al. | |
| 8,338,788 B2 | 12/2012 | Zilberstein et al. | |
| 8,492,725 B2 | 7/2013 | Zilberstein et al. | |
| 8,748,827 B2 | 6/2014 | Zilberstein et al. | |
| 9,606,245 B1 | 3/2017 | Czarnecki et al. | |
| 9,820,708 B2 | 11/2017 | Risher-Kelly | |
| 10,863,956 B2* | 12/2020 | Zilberstien | A61B 6/04 |
| 2003/0209662 A1 | 11/2003 | Nelson et al. | |
| 2005/0017182 A1 | 1/2005 | Joung et al. | |
| 2008/0217541 A1 | 9/2008 | Kim | |
| 2008/0230709 A1* | 9/2008 | Tkaczyk | G01T 1/249 |
| | | | 250/370.09 |
| 2010/0061509 A1 | 3/2010 | D'Ambrosio et al. | |
| 2010/0188082 A1 | 7/2010 | Morich et al. | |
| 2011/0026685 A1 | 2/2011 | Zilberstein et al. | |
| 2011/0103544 A1 | 5/2011 | Hermony | |
| 2013/0168567 A1 | 7/2013 | Wartski et al. | |
| 2013/0200269 A1* | 8/2013 | Abraham | G01T 1/1647 |
| | | | 250/395 |
| 2015/0028218 A1 | 1/2015 | Kataoka et al. | |
| 2015/0065874 A1 | 3/2015 | Rafaeli et al. | |
| 2015/0094571 A1 | 4/2015 | Bouhnik et al. | |
| 2015/0119704 A1 | 4/2015 | Roth et al. | |
| 2015/0276949 A1 | 10/2015 | Grobshtein et al. | |
| 2015/0342543 A1 | 12/2015 | Khen et al. | |
| 2016/0007941 A1 | 1/2016 | Hefetz | |
| 2016/0282153 A1* | 9/2016 | Hefetz | G21K 1/025 |
| 2016/0287197 A1* | 10/2016 | Risher-Kelly | A61B 6/4476 |
| 2016/0313263 A1 | 10/2016 | Featonby et al. | |
| 2016/0380728 A1 | 12/2016 | Dudek et al. | |
| 2017/0014096 A1 | 1/2017 | Bouhnik et al. | |
| 2017/0045632 A1* | 2/2017 | Thran | G01T 1/244 |
| 2017/0082759 A1 | 3/2017 | Lyu et al. | |
| 2017/0112454 A1 | 4/2017 | Yun et al. | |
| 2017/0153338 A1 | 6/2017 | Kovalski et al. | |
| 2017/0189720 A1 | 7/2017 | Liu et al. | |
| 2017/0332025 A1 | 11/2017 | Nozawa et al. | |
| 2017/0370499 A1* | 12/2017 | Fujimoto | F16K 31/04 |
| 2018/0059270 A1 | 3/2018 | Hefetz et al. | |
| 2018/0110496 A1 | 4/2018 | Levy et al. | |
| 2018/0236267 A1* | 8/2018 | Kuang | A61B 6/5235 |
| 2020/0163631 A1 | 5/2020 | Okuno | |
| 2020/0281546 A1 | 9/2020 | Zilberstien et al. | |
| 2020/0289074 A1 | 9/2020 | Zilberstien et al. | |
| 2020/0297296 A1 | 9/2020 | Zilberstien et al. | |
| 2020/0301033 A1 | 9/2020 | Roth et al. | |

FOREIGN PATENT DOCUMENTS

| | | |
|---|---|---|
| WO | WO 2019/077542 | 4/2019 |
| WO | WO 2019/077542 A3 | 4/2019 |
| WO | WO 2019/077544 | 4/2019 |
| WO | WO 2019/077548 | 4/2019 |
| WO | WO 2019/077548 A3 | 4/2019 |
| WO | WO 2019/077552 | 4/2019 |

OTHER PUBLICATIONS

Supplementary European Search Report and the European Search Opinion dated Jun. 9, 2021 From the European Patent Office Re. Application No. 18868387.4. (7 Pages).

International Preliminary Report on Patentability dated Apr. 30, 2020 From the International Bureau of WIPO Re. Application No. PCT/IB2018/058094. (7 Pages).

International Preliminary Report on Patentability dated Apr. 30, 2020 From the International Bureau of WIPO Re. Application No. PCT/IB2018/058097. (6 Pages).

International Preliminary Report on Patentability dated Apr. 30, 2020 From the International Bureau of WIPO Re. Application No. PCT/IB2018/058102. (8 Pages).

International Preliminary Report on Patentability dated Apr. 30, 2020 From the International Bureau of WIPO Re. Application No. PCT/IB2018/058108. (10 Pages).

International Search Report and the Written Opinion dated Apr. 23, 2019 From the International Searching Authority Re. Application No. PCT/IB2018/058108. (20 Pages).

International Search Report and the Written Opinion dated Apr. 24, 2019 From the International Searching Authority Re. Application No. PCT/IB2018/058094. (15 Pages).

International Search Report and the Written Opinion dated Apr. 24, 2019 From the International Searching Authority Re. Application No. PCT/IB2018/058102. (16 Pages).

International Search Report and the Written Opinion dated Feb. 25, 2019 From the International Searching Authority Re. Application No. PCT/IB2018/058097. (12 Pages).

Invitation to Pay Additional Fees dated Feb. 7, 2019 From the International Searching Authority Re. Application No. PCT/IB2018/058094. (2 Pages).

Invitation to Pay Additional Fees dated Feb. 7, 2019 From the International Searching Authority Re. Application No. PCT/IB2018/058102. (3 Pages).

Invitation to Pay Additional Fees dated Feb. 7, 2019 From the International Searching Authority Re. Application No. PCT/IB2018/058108. (2 Pages).

Notice of Allowance dated Aug. 12, 2020 from the US Patent and Trademark Office Re. U.S. Appl. No. 16/756,492. (9 pages).

Official Action dated Sep. 9, 2020 from the US Patent and Trademark Office Re. U.S. Appl. No. 16/756,496. (27 pages).

Supplementary European Search Report and the European Search Opinion dated Jun. 21, 2021 From the European Patent Office Re. Application No. 18869300.6. (8 Pages).

Interview Summary dated Mar. 19, 2021 From the US Patent and Trademark Office Re. U.S. Appl. No. 16/756,496. (2 Pages).

Supplementary European Search Report and the European Search Opinion dated Jun. 4, 2021 From the European Patent Office Re. Application No. 18868897.2. (7 Pages).

Final Official Action dated Feb. 23, 2021 From the US Patent and Trademark Office Re. U.S. Appl. No. 16/756,496. (25 Pages).

Official Action dated Jul. 7, 2021 from the US Patent and Trademark Office Re. U.S. Appl. No. 16/756,496. (12 pages).

Supplementary European Search Report and the European Search Opinion dated Jul. 14, 2021 From the European Patent Office Re. Application No. 18869177.8. (8 Pages).

Notice of Allowance dated Jan. 21, 2022 together eoth Interview Summary dated Jan. 6, 2022 from US Patent and Trademark Office Re. U.S. Appl. No. 16/756,511. (8 pages).

Final Office Action dated Sep. 20, 2021 from the US Patent and Trademark Office Re. U.S. Appl. No. 16/756,511. (26 pages).

Restriction Official Action dated Apr. 2, 2021 From the US Patent and Trademark Office Re. U.S. Appl. No. 16/756,511. (6 Pages).

Almeida Silva Salvado "Evaluation of the D-SPECT System: Geometry Considerations and Respiratory Motion", Dissertação Mestrado Integrado em Engenharia Biomédica e Biofísica, Perfil de Radiações em Diagnóstico e Terapia [Dissertation Integrated Master in Biomedical Engineering and Biophysics, Radiation Profile in Diagnosis and Therapy], Universidade de Lisboa, Portugal, Faculdade de Ciências Departamento de Física, 134 P., 2012.

Barrento Da Costa "Evaluation of the D-SPECT System: Region Centric Acquisition and Tracer Kinetics", Dissertação Mestrado Integrado em Engenharia Biomédica e Biofísica [Dissertation Integrated Master in Biomedical Engineering and Biophysics], Universidade de Lisboa, Portugal, Faculdade de Ciências, Departamento de Física, 97 P., 2012.

(56) References Cited

OTHER PUBLICATIONS

Erlandsson et al. "Assessing Possible Use of CZT Technology for Application to Brain SPECT", 2011 IEEE Nuclear Science Symposium Conference Record, Valencia, Spain, Oct. 23-29, 2011, p. 3354-3358, Oct. 23, 2011.
Gambhir et al. "A Novel High-Sensitivity Rapid-Acquisition Single-Photon Cardiac Imaging Camera", The Journal of Nuclear Medicine, 50(4): 635-643, Apr. 2009.
Moore et al. "Improved Performance From Modifications to Multidetector SPECT Brain Scanner", The Journal of Nuclear Medicine, 25(6): 688-691, Jun. 1984.
Slomka et al. "Advances in Technical Aspects of Myocardial Perfusion SPECT Imaging", Journal of Nuclear Cardiology, 16(2): 255-276, Published Online Feb. 26, 2009.

* cited by examiner

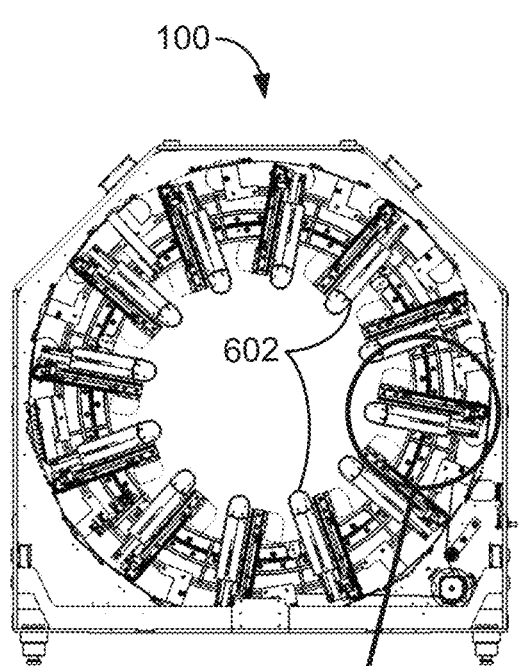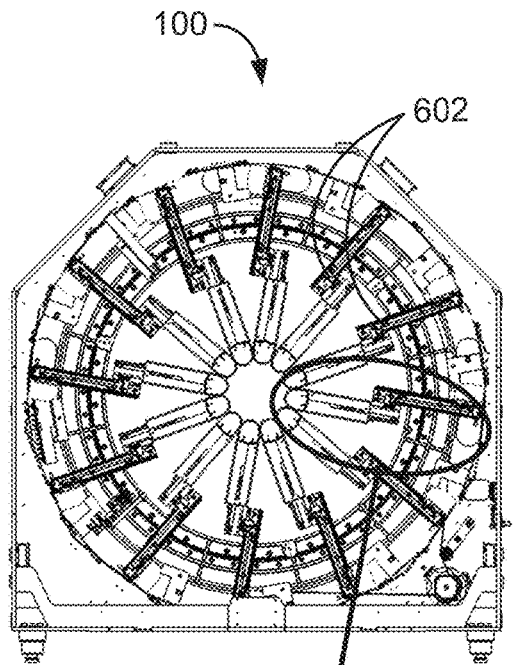
FIG. 6A  FIG. 6B
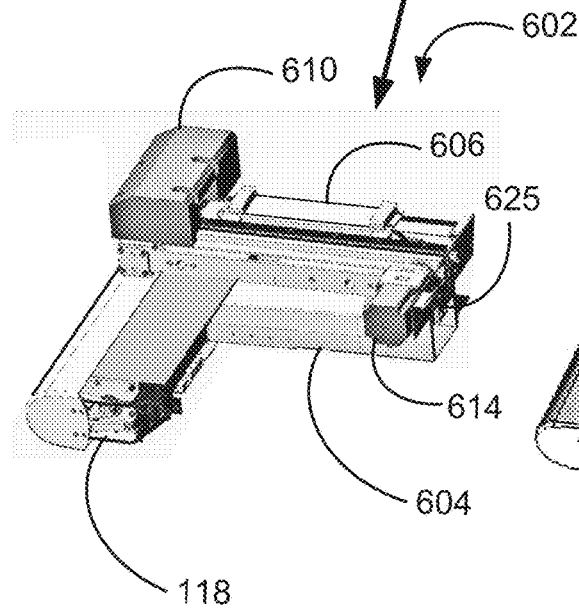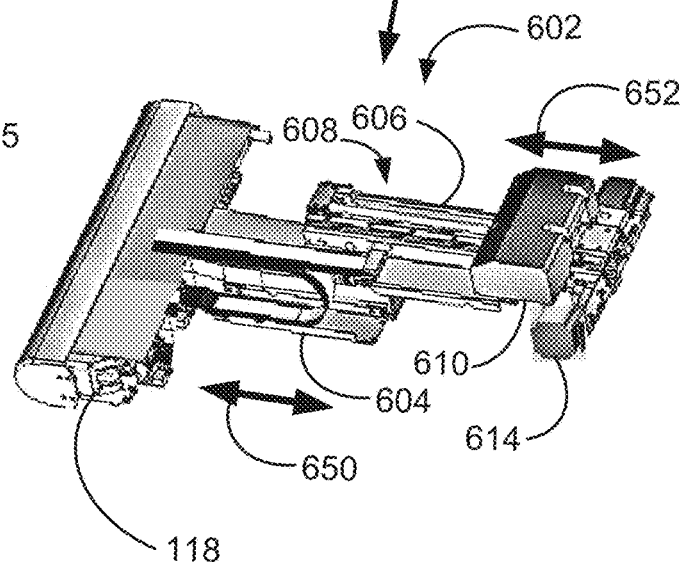
FIG. 6C  FIG. 6D

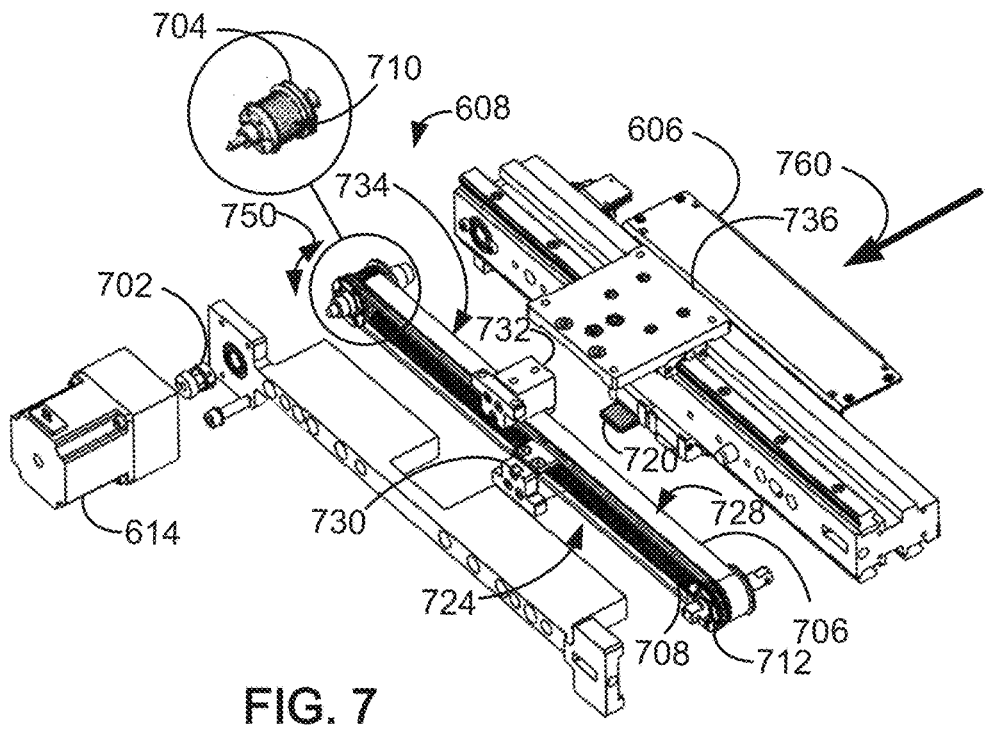
FIG. 7
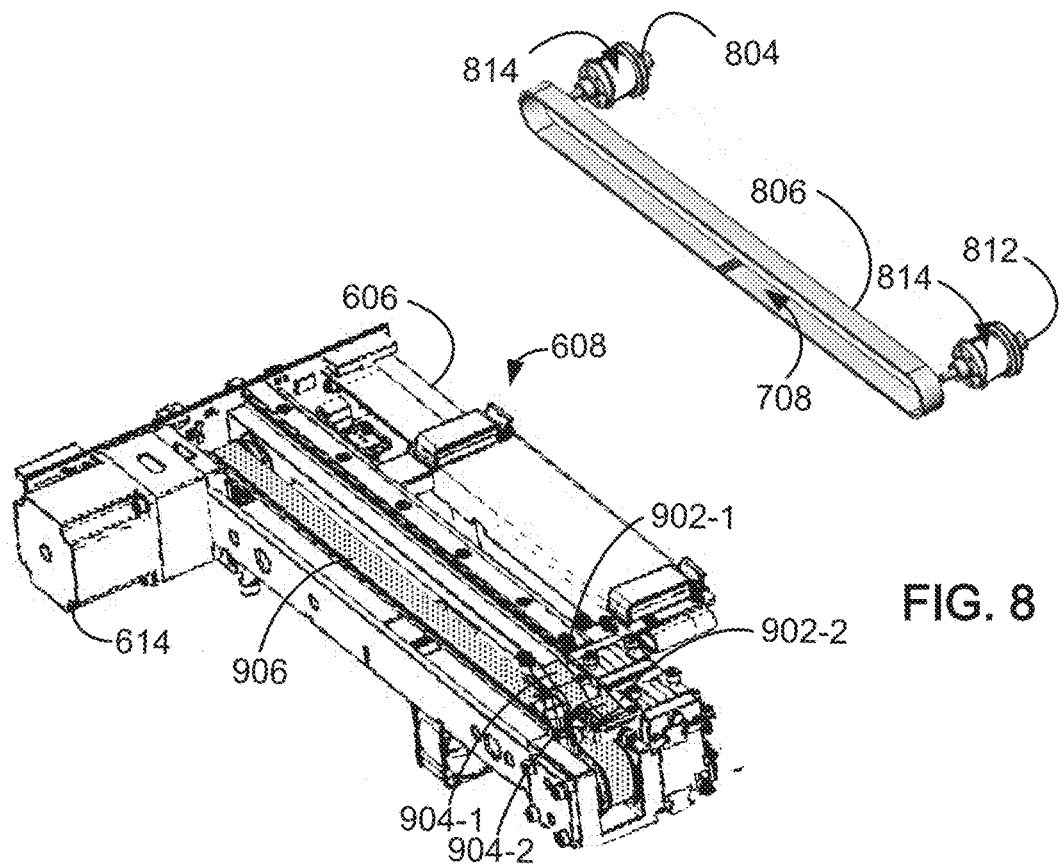
FIG. 8
FIG. 9

MOVING PARTS IN A NUCLEAR MEDICINE (N-M) IMAGING SYSTEM

RELATED APPLICATIONS

This application is a continuation of U.S. patent application Ser. No. 16/756,492 filed on Apr. 16, 2020, which is a National Phase of PCT Patent Application No. PCT/IB2018/058097 having International Filing Date of Oct. 18, 2018, which claims the benefit of priority under USC § 119(e) of U.S. Provisional Patent Application No. 62/574,277 filed on Oct. 19, 2017. The contents of the above applications are all incorporated by reference as if fully set forth herein in their entirety.

PCT Patent Application No. PCT/IB2018/058097 is also related to co-filed, co-pending and co-assigned:

International Patent Application No. PCT/IB2018/058102 filed on Oct. 18, 2018 entitled "COOLING OF A NUCLEAR MEDICINE TOMOGRAPHY SYSTEM" which claims the benefit of priority of U.S. Provisional Patent Application No. 62/574,345 filed on Oct. 19, 2017, International Patent Application No. PCT/IB2018/058108 filed on Oct. 18, 2018 entitled "CALIBRATION AND QUALITY CONTROL OF A NUCLEAR-MEDICINE (N-M) RADIO IMAGING SYSTEM" which claims the benefit of priority of U.S. Provisional Patent Application No. 62/574,300 filed on Oct. 19, 2017, and International Patent Application No. PCT/IB2018/058094 filed on Oct. 18, 2018 entitled "SAFETY MECHANISMS FOR CLOSE RANGE TOMOGRAPHIC SCANNING MACHINE AND METHODS OF USE" which claims the benefit of priority of U.S. Provisional Patent Application No. 62/574,294 filed on Oct. 19, 2017, the contents of which are all incorporated by reference as if fully set forth herein in their entirety.

PCT Patent Application No. PCT/IB2018/058097 is also related to US Patent Publication No. 2015/0119704, U.S. Pat. Nos. 8,338,788, 8,492,725 and 8,748,827 the contents of which are all incorporated by reference as if fully set forth herein in their entirety.

FIELD AND BACKGROUND OF THE INVENTION

The present invention, in some embodiments thereof, relates to Nuclear Medicine Imaging devices and, more particularly, but not exclusively, to moving parts in a Nuclear Medicine Imaging device.

Nuclear medicine involves application of radioactive substances in the diagnosis and treatment of disease. Nuclear Medicine Imaging devices, e.g., Single Photon Emission Computed Tomography (SPECT) and Positron Emission Tomography (PET) scanners are designed to record radiation emitting from within the body and generate an image corresponding to the recorded emission.

SUMMARY OF THE INVENTION

According to an aspect of some embodiments of the present invention there is provided a Nuclear Medicine (N-M) imaging system gantry including at least one stationary stator, at least one rotor rotatably mounted on the stator and including at least one detection unit having at least one Multi-Pixel Photon Counter (MPC) and at least one rotor driving assembly including at least one motor and a flat driving belt mounted on a peripheral flat surface of the rotor and driven by the motor.

According to some embodiments, the rotor driving assembly motor includes an output axis and a pulley mounted on the shaft and the belt is an open belt having two ends. According to some embodiments, each of the belt ends is coupled to a respective clamp fixedly attached to the circumference of the rotor and a length of the belt is equal to or shorter than a circumference of the rotor.

According to some embodiments, the rotor driving assembly includes at least one driving belt tensioning system that includes at least one pivotable tensioning arm and a pulley.

According to some embodiments, the N-M imaging system includes at least one controller in communication with at least the rotor driving assembly and a level of friction between the belt and the circumferential surface is controlled by the controller. The controller controls the level of friction between the belt and the circumferential surface by controlling degree of pivot of the tensioning arm. According to some embodiments, the tensioning system includes a driving belt tension sensor in communication with the controller and provides the controller with feedback information regarding the level of tension in the driving belt. According to some embodiments, the sensor includes an ultrasound sensor.

According to some embodiments, the driving belt tensioning system is controlled manually or automatically.

According to some embodiments, the rotor includes one or more stoppers that include a mechanical stopper having a first lever mounted on the rotor and a second lever positioned on the stator. The levers unidirectionally interferes with a path of travel of the other lever as the rotor rotates in a first direction and allows the rotor to rotate in an opposite second direction. The rotor includes a first rotation direction stopper and a second rotation direction stopper. The stoppers block rotation of the rotor when at least one of the clamps approaches the rotor driving assembly.

According to some embodiments, the gantry includes a rotor rotation linear encoder in communication with the controller and provides the controller with feedback information regarding spatial position of the rotor at any point along the rotor path of rotor rotation and includes at least one sensor and at least one scale strip.

According to some embodiments, the scale strip includes a magnetic scale strip. According to some embodiments, the encoder includes an optical encoder.

According to some embodiments, the encoder sensor is coupled to the stator and the scale moves across the sensor as the rotor rotates. According to some embodiments, the encoder is positioned on or after the output axis of the rotor driving assembly.

According to an aspect of some embodiments of the present invention there is provided a Nuclear Medicine (N-M) imaging system gantry including at least one stationary stator, at least one rotor rotatably mounted on the stator and including at least one detection unit including at least one stationary chassis, at least one extendable arm movably coupled to the chassis, at least one scanning column having at least one Multi-Pixel Photon Counter (MPC) mounted on the extendable arm, and at least one linear drive system that extends and retracts the extendable arm radially inward and outwards in respect to the rotor.

According to some embodiments, the N-M imaging system includes at least one controller and the linear drive system includes at least one motor in bidirectional communication with the controller. The linear drive system is configured to bidirectionally and axially move the extendable arm in a stepwise fashion and to stop at any point in accordance with input from controller.

According to some embodiments, the linear drive system includes at least one driver pulley coupled to an output axis of the motor and an idler pulley, both pulleys mounted along the chassis and at a distance between them. According to some embodiments, the linear drive system includes a driving belt mounted on the driver pulley and the idler pulley and the driving belt includes an open belt having two ends, each of the belt ends is coupled to a respective clamp fixedly attached to the extendable arm.

According to some embodiments, the linear drive system includes at least one driving belt tensioning system. According to some embodiments, a surface of the linear drive system driver pulley and a surface of the driving belt in contact with driver pulley surface are ribbed. According to some embodiments, the linear drive system includes at least one linear encoder in communication with the controller and provides the controller with feedback information regarding spatial position of the extendable arm at any point along the arm axial path of movement. The encoder includes at least one sensor and at least one scale strip. According to some embodiments, the scale strip includes a magnetic scale strip. According to some embodiments, the encoder includes an optical encoder. According to some embodiments, the encoder sensor is coupled to the chassis and the scale moves across the sensor as the extendable arm extends and retracts. According to some embodiments, the encoder is positioned on or after the output axis of the linear drive system.

According to an aspect of some embodiments of the present invention there is provided a Nuclear Medicine (N-M) imaging system including at least one controller and at least one gantry including at least one stationary stator, at least one rotor rotatably mounted on the stator and including at least one detection unit having at least one Multi-Pixel Photon Counter (MPC), the rotor driven by at least one rotor driving assembly and at least one detection unit mounted on the rotor and including at least one scanning column having at least one Multi-Pixel Photon Counter (MPC) mounted on at least one extendable arm and at least one flat cable connected on one end to the controller and on another end to at least the scanning column Multi-Pixel Photon Counter (MPC).

According to some embodiments, the flat cable includes a plurality of data cables. According to some embodiments, the Nuclear Medicine (N-M) imaging system includes a source of electrical power and wherein the flat cable conducts electrical power to at least the scanning column Multi-Pixel Photon Counter (MPC).

According to some embodiments, the detector unit includes a chassis having at least one data information connector configured to connect one or more data information cables originating from the controller and at least one detection unit flat data cable. According to some embodiments, the at least one detector unit flat data cable is connected on one end to the chassis connector and on the other end to at least the scanning column Multi-Pixel Photon Counter (MPC). According to some embodiments, the flat cable is configured to flex and move along a single-dimension during axial reciprocating motion of the extendable arm in respect to the chassis.

According to an aspect of some embodiments of the present invention there is provided a Nuclear Medicine (N-M) imaging system including at least one gantry including at least one stationary stator, at least one rotor rotatably mounted on the stator and including at least one detection unit including at least one pivotable scanning column having at least one Multi-Pixel Photon Counter (MPC), the pivotable scanning column driven by at least one scanning column driver assembly.

According to some embodiments, the at least one scanning column is configured to pivot bidirectionally about the longitudinal axis of the scanning column at least partially along a circular path of less than 360 degrees. According to some embodiments, the N-M imaging system includes at least one controller and the scanning column driver assembly includes at least one motor in communication with and controlled by the controller. The scanning column driver assembly includes at least one scanning column pivot rotary encoder and the rotary encoder includes at least one sensor and at least one scale disc.

According to some embodiments, the rotary encoder is in communication with the controller and provides the controller with feedback information regarding spatial position of the scanning column at any point along the column path of pivot. According to some embodiments, the rotary encoder scale disc includes a magnetic scale disc. According to some embodiments, the rotary encoder scale disc includes an optical encoder.

According to some embodiments, the encoder scale disc is mounted on or after an output axis of the scanning column driving assembly motor. According to some embodiments, the driving belt includes at least one first coupling for attaching to the extendable arm and at least one second coupling to couple to a counter weight carrier. According to some embodiments, the first coupling and second coupling are positioned on opposite sides of the driving belt. According to some embodiments, the extendable arm carrying the scanning unit and the counter weight are positioned on opposite sides of the driving belt. According to some embodiments, a longitudinal axis of a wide aspect of the counter weight parallels a longitudinal axis of the scanning unit.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, some embodiments of the present invention may be embodied as a system, method or computer program product. Accordingly, some embodiments of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a system, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Some of the methods described herein are generally designed only for use by a computer, and may not be feasible or practical for performing purely manually, by a human expert. A human expert, who wanted to manually perform similar tasks, might be expected to use completely different methods, e.g., making use of expert knowledge and/or the pattern recognition capabilities of the human brain, which would be vastly more efficient than manually going through the steps of the methods described herein.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 6A, 6B, 6C and 6D are side view simplified illustrations of arrangement of an N-M imaging system detection units in an N-M imaging system gantry and a perspective view simplified illustration of a detection unit head and extendable arm in accordance with some embodiments of the invention;

FIG. 7 is a perspective exploded view simplified illustration of an N-M imaging system detection unit linear drive system in accordance with some embodiments of the invention;

FIG. 8 is a perspective view simplified illustration of a detection unit linear drive system in accordance with some embodiments of the invention;

FIG. 9 is a perspective exploded view simplified illustration of a detection unit linear drive system 608 in accordance with some embodiments of the invention;

DESCRIPTION OF SPECIFIC EMBODIMENTS OF THE INVENTION

Figure 1:
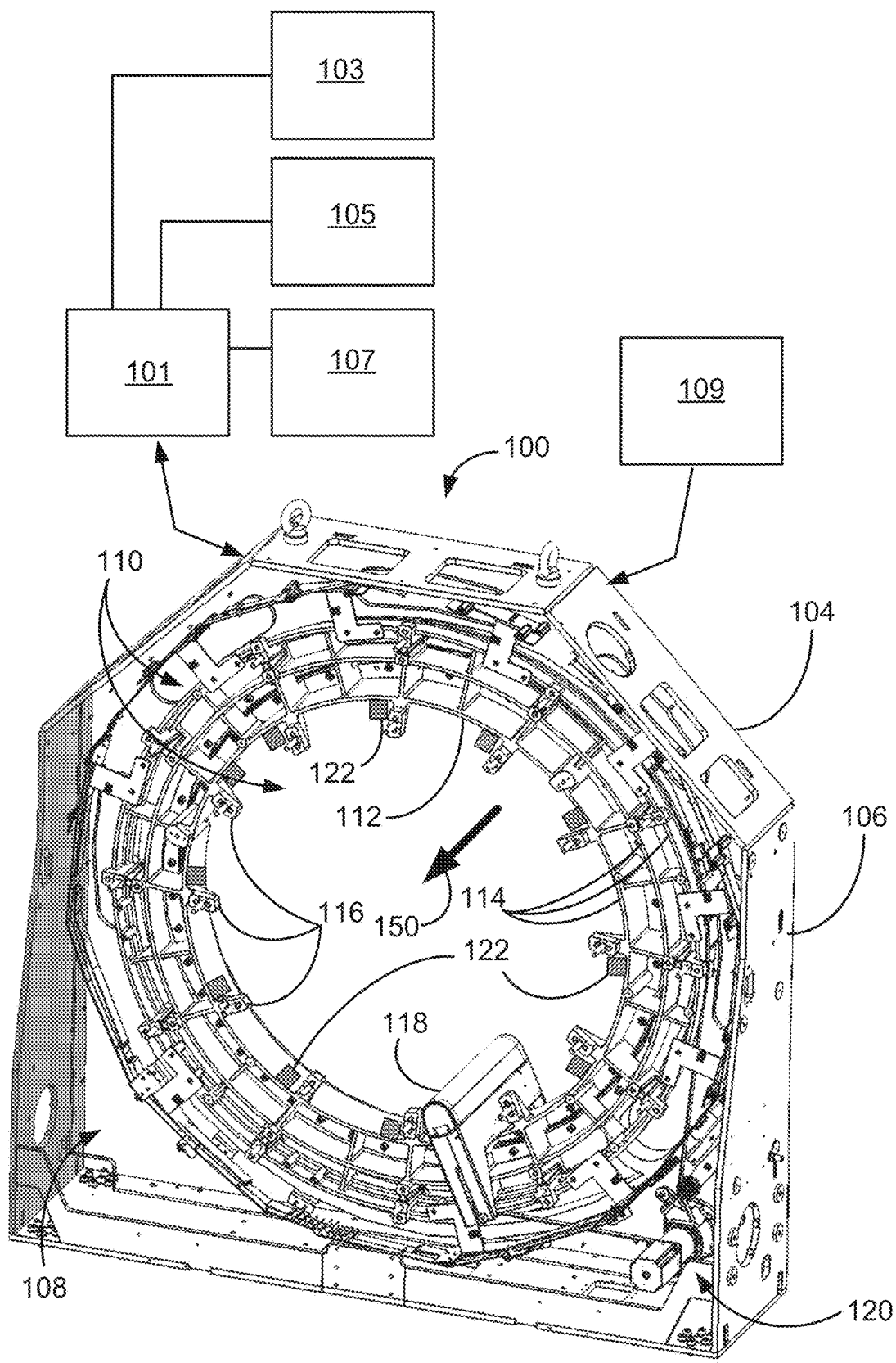
FIG. 1 is a part diagram and perspective view simplified illustration of a Nuclear Medicine (N-M) imaging system in accordance with some embodiments of the invention.

The present invention, in some embodiments thereof, relates to Nuclear Medicine Imaging devices and, more particularly, but not exclusively, to moving parts in a Nuclear Medicine Imaging device.

An aspect of some embodiments of the invention relates to a Nuclear Medicine (N-M) imaging system gantry comprising at least one stator and at least one rotor and a rotor driving assembly.

In some embodiments, the rotor driving assembly comprises a flat driving belt. In some embodiments, the flat belt comprises at least one smooth side. In some embodiments, the driving belt smooth side is positioned in contact with a circumferential flat surface of the rotor.

In some embodiments, the driving belt comprises an open belt having two ends. In some embodiments, the ends of the driving belt are coupled to respective clamps. In some embodiments, the clamps are fixedly attached to the outer circumferential flat surface of the rotor.

In some embodiments, the rotor driving assembly comprises at least one tensioning system including at least one tensioning arm. In some embodiments, the tensioning arm is pivotable. In some embodiments, the tensioning arm is controlled by a controller. In some embodiments, the pivotable tensioning arm comprises a pulley. In some embodiments, the pulley is an idle pulley. In some embodiments, the rotor driving assembly comprises a tension sensor.

In some embodiments, the rotor driving assembly comprises one or more stoppers. In some embodiments, the stoppers are mechanical. In some embodiments, the stoppers comprise a first lever mounted on the rotor and a second lever positioned on the stator. In some embodiments, the gantry rotor comprises a first rotation direction stopper and a second rotation direction stopper.

An aspect of some embodiments of the invention relates to a Nuclear Medicine (N-M) imaging system gantry comprising at least one stator and at least one rotor and at least one rotor movement encoder. In some embodiments, the encoder comprises a linear encoder. In some embodiments, the linear encoder comprises one or more sensors and a scale strip. In some embodiments and optionally, the linear encoder comprises a magnetic scale strip. In some embodiments and alternatively and optionally, the encoder comprises an optical encoder and scale strip. In some embodiments, the sensor comprises a sensor flag. In some embodiments, the sensor is coupled to the stator in a stationary position and the scale moves across the sensor as the rotor rotates. In some embodiments and optionally, the scale is disposed along a circumferential surface of rotor.

An aspect of some embodiments of the invention relates to a Nuclear Medicine (N-M) imaging system gantry comprising at least one stator and at least one rotor having one or more detection units carried by one or more extendable detection arms, each extendable detection arm extendable by an extendable arm driving system. In some embodiments, the extendable arm is movable from a fully retracted (Home) position to a fully extended position. In some embodiments, the extendable arm driving system comprises a linear drive system. In some embodiments, the linear drive system is in bidirectional communication with the controller. In some embodiments, the linear drive system moves the extendable arm and a scanning unit in a stepwise fashion.

In some embodiments, the linear drive system comprises one or more motors and one or more driving belts positioned on one or more pulleys. In some embodiments, at least one pulley is a belt driver pulley. In some embodiments, at least one pulley is an idler pulley. In some embodiments, the linear driving system motor rotates the belt driver pulley in a clockwise or counter clockwise in a continuous or stepped motion. In some embodiments, the one or more pulleys comprise a ribbed surface, which corresponds to a ribbed inner surface of the driving belt.

In some embodiments, the driving belt comprises at least one surface and is driven by a driver pulley having a flat surface. In some embodiments, the linear driving system comprises at least one tensioning arm. In some embodiments, the tensioning arm is pivotable. In some embodiments, the tensioning arm is controlled by a controller. In some embodiments, the pivotable tensioning arm comprises a pulley. In some embodiments, the pulley is an idle pulley. In some embodiments, the linear drive system comprises a tension sensor.

In some embodiments, the linear drive system comprises a looped belt mounted on the driving pulley and the idler pulley. In some embodiments, one or both pulleys are coupled to a stationary portion (e.g., chassis) of the extendable arm by adjustable couplings that allow adjusting the distance between the pulleys thereby adjusting tension of the belt mounted on the pulleys. In some embodiments, the linear driving system comprises a belt tension sensor in communication with the controller. In some embodiments, the tension sensor comprises an ultrasound sensor. Alternatively and optionally, in some embodiments the linear drive system comprises an arm system. In some embodiments, the tensioning system comprises a tensioning arm and a pulley.

In some embodiments, the linear drive system driving belt comprises an open flat belt having two ends. In some embodiments and optionally, the driving belt comprises a closed ring.

An aspect of some embodiments of the invention relates to a Nuclear Medicine (N-M) imaging system gantry comprising at least one stator and at least one rotor having one or more detection units including one or more flat data and power cables. In some embodiments, the flat cables transfer data and power between system components (e.g., the chassis and the extendable arm).

In some embodiments, the flat cable comprises a double-layered flat cable carrying both power and data. In some embodiments, the flat cable comprises one end attached to the detection unit chassis and a second end is attached to the detection unit extendable arm. In some embodiments, the flat cable flexes with a rolling-flex axial movement along an axis of movement (X) of the extendable arm with little or no lateral movement along an axis (R) perpendicular to axis (X).

An aspect of some embodiments of the invention relates to a Nuclear Medicine (N-M) imaging system gantry comprising at least one detection unit comprising at least one column mounted on an extendable arm. In some embodiments, the extendable arm is axially moveable and extendable along and from a stationary chassis. In some embodiments, the detection unit comprises a linear encoder. In some embodiments, the linear encoder comprises a sensor and a scale strip. In some embodiments and optionally, the linear encoder comprises a magnetic scale strip. Alternatively and optionally, the detection unit comprises an optical encoder and scale strip. In some embodiments, the sensor comprises a sensor flag. In some embodiments, sensor is coupled to the chassis, which remains in a stationary position in respect to extendable arm. In some embodiments and optionally, the scale is disposed along the chassis and the sensor is coupled to and moves with the extendable arm.

An aspect of some embodiments of the invention relates to a Nuclear Medicine (N-M) imaging system gantry comprising at least one detection unit comprising at least one pivotable column mounted on an extendable arm and a rotation driver assembly including a rotary encoder. In some embodiments, the rotation driver assembly comprises a motor. In some embodiments, the motor is configured to pivot the column bidirectionally at least partially along a circular path of less than 360 degrees, 300 degrees, 270 degrees, 210 degrees, 150 degrees, or any intermediate angle around a pivot axis (P) parallel to the longitudinal axis of the scanning column. In some embodiments, one or more scanning columns comprises Multi-Pixel Photon Counters (MPCs). In some embodiments, the motor generates a stepped rotational mechanical driving force effected on the scanning columns via a gearbox.

In some embodiments, the rotation driver assembly includes a rotary encoder comprising a sensor and a circular scale strip. Optionally the rotary encoder comprises a magnetic scale strip. Alternatively and optionally, the scanning column comprises an optical rotary encoder and scale strip. In some embodiments, the sensor comprises a sensor flag. In some embodiments, the sensor is coupled to the scanning column driver assembly chassis, which remains in a stationary position in respect to the scanning columns. In some embodiments, the scale disc is coupled to an output axis proximally to the coupling and moves across the sensor.

As used herein, the terms "Circumferential Movement" or "Circumferentially" refers to rotation of the gantry (e.g., rotor) and also includes movement of the detector heads on the gantry upon rotation of the rotor. Likewise, circumferential movement includes translational movement of each of the detector heads individually, i.e., independently, or in groups within the rotor, and/or movement of the entire rotor relative to other rings or the stator. As used herein, the terms "Axial Movement" or "Axially" refer to movement along a central axis of rotation of the rotor, perpendicular to a plane defined by the rotor.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Exemplary Nuclear Medicine Imaging System

Referring now to the drawings, FIG. 1 is a part diagram and perspective view simplified illustration of a Nuclear Medicine (N-M) imaging system in accordance with some embodiments of the invention. In some embodiments, the N-M imaging system communicates with a controller 101 and via controller 101 with one or more monitors 103, one or more input systems 105, e.g., a touch screen or keypad and a patient table 107. N-M imaging system also comprises or is connected to one or more sources of electrical power 109.

In the exemplary embodiment depicted in FIG. 1, N-M imaging system comprises a gantry 100 including a stator 104 and a rotor 112 that carries one or more scanning units 118.

In some embodiments, stator 104 comprises non-moving parts such as, for example, a fixed chassis 106 comprising one or more plates 108 coupled to chassis 106 on one or both sides. In some embodiments, walls 108 include one or more openings 110 at least one of which sized and fitted to receive a patient table (not shown). In some embodiments, rotor 112 comprises gantry 100 moving parts such as, for example, scanning units 118 mounted on one or more detection units 102. In some embodiments, rotor 112 comprises a ring circumferentially rotatable in one or more circumferential directions and driven by a rotor driving assembly 120. In some embodiments, rotor 112 comprises one or more structural support rings 114. In some embodiments, rotor 112 comprises one or more detection unit couplings 116 for coupling one or more extendable arm 604 (FIGS. 6A-D) and Scanning unit 118 to rotor 112.

In some embodiments, extendable arm 604 comprise linear drive mechanisms that drive Scanning units 118 radially inwards or radially outwards in respect to rotor 112 as explained in greater detail elsewhere herein. In the exemplary embodiment depicted in FIG. 1 all but one detection unit have been removed in the interest of clarity.

In some embodiments, N-M imaging system comprises support legs and/or is fixed to a floor. In some embodiments, N-M imaging system is supported by a moveable dolly having adjustable and/or lockable wheels (not shown).

Exemplary Rotor Movement and Rotor Driving System

Figure 2:
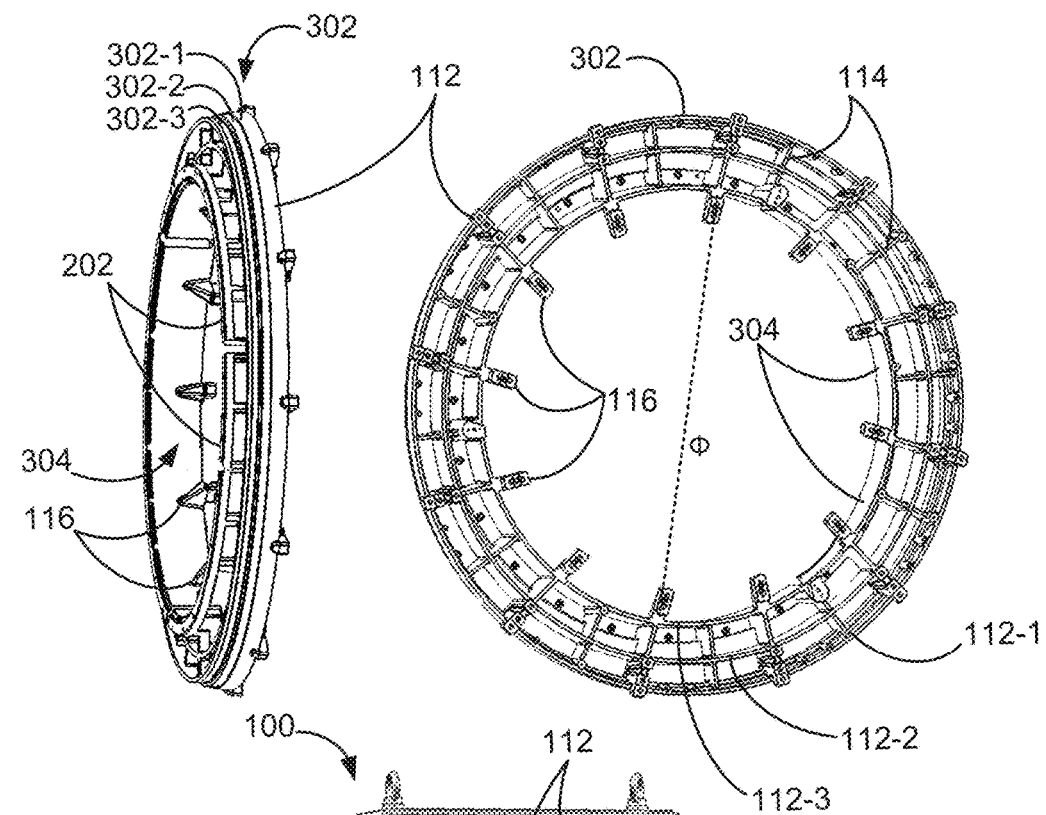
FIG. 2 is a front view and perspective view simplified illustration of an N-M imaging system gantry rotor in accordance with some embodiments of the invention.
Figure 3:
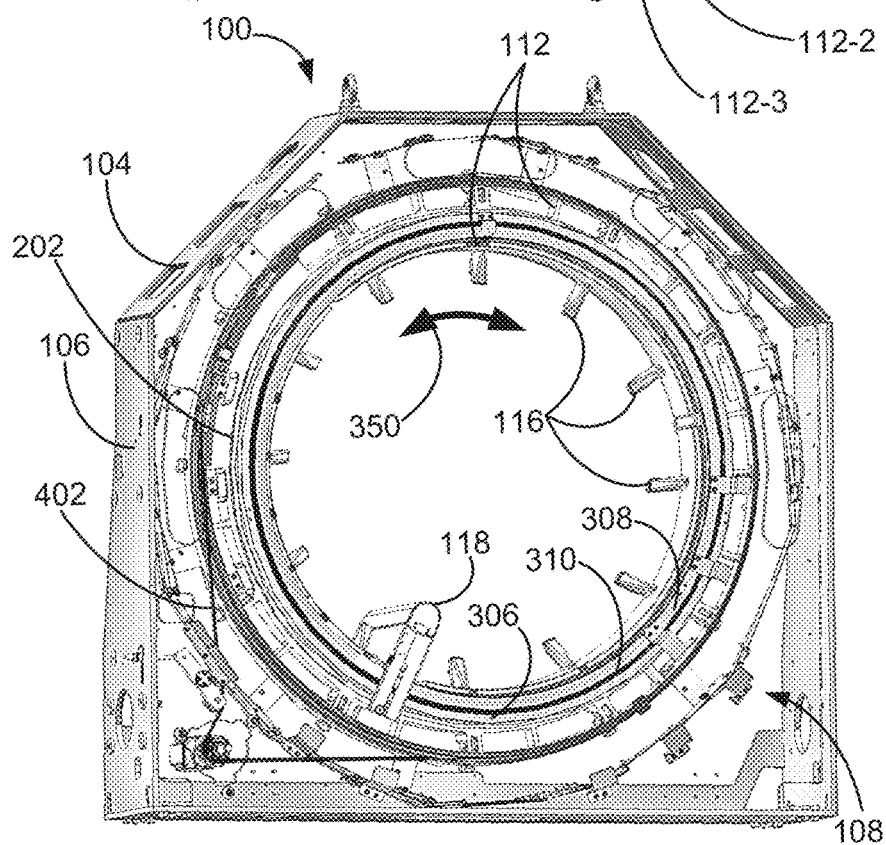
FIG. 3 is a perspective view simplified illustration of an N-M imaging system rotor integrated into an N-M imaging system gantry in accordance with some embodiments of the invention.

Reference is now made to FIG. 2, which is a front view and perspective view simplified illustration of an N-M imaging system gantry rotor and FIG. 3, which is a perspective view simplified illustration of an N-M imaging system rotor integrated into an N-M imaging system gantry in accordance with some embodiments of the invention. In the exemplary embodiment depicted in FIG. 2, rotor 112 comprises one or more rings 112-1, 112-2 and 112-3. Optionally, in some embodiments, rotor 112 comprises two or more concentric rings attached to each other by one or more radially oriented structural support rings 114. In some embodiments, rotor 112 comprises one or more scanning head attachments 116 for coupling one or more detection units to rotor 112.

In some embodiments, rotor 112 comprises one or more outer circumferential surfaces 302 and one or more centrally facing inner surfaces 304. In some embodiments, one or more outer circumferential surfaces 302 comprise flat surfaces.

In some embodiments, rotor 112 comprises a rotor mounting ring 202 that protrudes axially from centrally facing inner surface 304 beyond edges of rotor 112 one or more rings. Mounting ring 202 comprises couplings configured to couple ring 202 to bearing 310 as explain elsewhere herein.

In the exemplary embodiment depicted in FIG. 3, which is perspective view simplified illustration of N-M imaging system as viewed from a direction indicated in FIG. 1 by an arrow designated reference numeral 150, at least a portion of outer circumferential surface 302 is flat and configured to receive a driving belt 402. In some embodiments, outer circumferential surface 302 comprises a stepped cross section comprises one or more flat steps 302-1, 302-2, 302-3 at least one sized to receive driving belt 402. In some embodiments, outer circumferential surface 302 comprises a groove (not shown) having a flat floor configured to receive driving belt 402. In some embodiments, alternatively and optionally, outer circumferential surface 302 may comprise cogs (not shown) so that to form a cog wheel driven by a cogwheel driver, e.g. a motor or ribbed driving belt.

In some embodiments, rotor 112 is rotationally coupled to a bearing 302. In some embodiments, bearing 310 comprises a slewing bearing. In some embodiments, bearing 310 comprises a low-friction bearing enabling a low power motor to drive gantry 100 rotor 112. In the exemplary embodiment shown in FIG. 3, bearing 310 comprises an outer race 306 concentrically surrounding an inner race 308. Inner race 308 defines an aperture sized to correspond at least to inner diameter (Φ) of rotor 112. In the exemplary embodiment shown in FIG. 3, outer race 306 is fixedly coupled to a ring-shaped stator plate 108 that renders outer race 306 stationary. Rotor 112 mounting ring 202 is fixedly coupled to inner race 308 and is freely circumferentially rotatable in clockwise or counter-clockwise directions as indicated by a double-headed arrow 350. In some embodiments, rotor 112 rotates less than 360 degrees in either direction. In some embodiments, rotor 112 rotates a maximum circumferential rotation of 350, or 300, or 250, or 200, or 150, or 100 degrees in each direction, more than 350 degrees or any number in between. In some embodiments, rotor 112 rotates less than 210 degrees in either direction. In some embodiments, rotor 112 rotation comprises a stepped circumferential movement.

Alternatively and optionally, inner race 308 is fixedly coupled to a ring-shaped stator plate 108 that renders inner race 308 stationary. Rotor 112 mounting ring 202 is fixedly coupled to outer race 306 and is freely circumferentially rotatable in clockwise or counter-clockwise directions.

Figure 4:
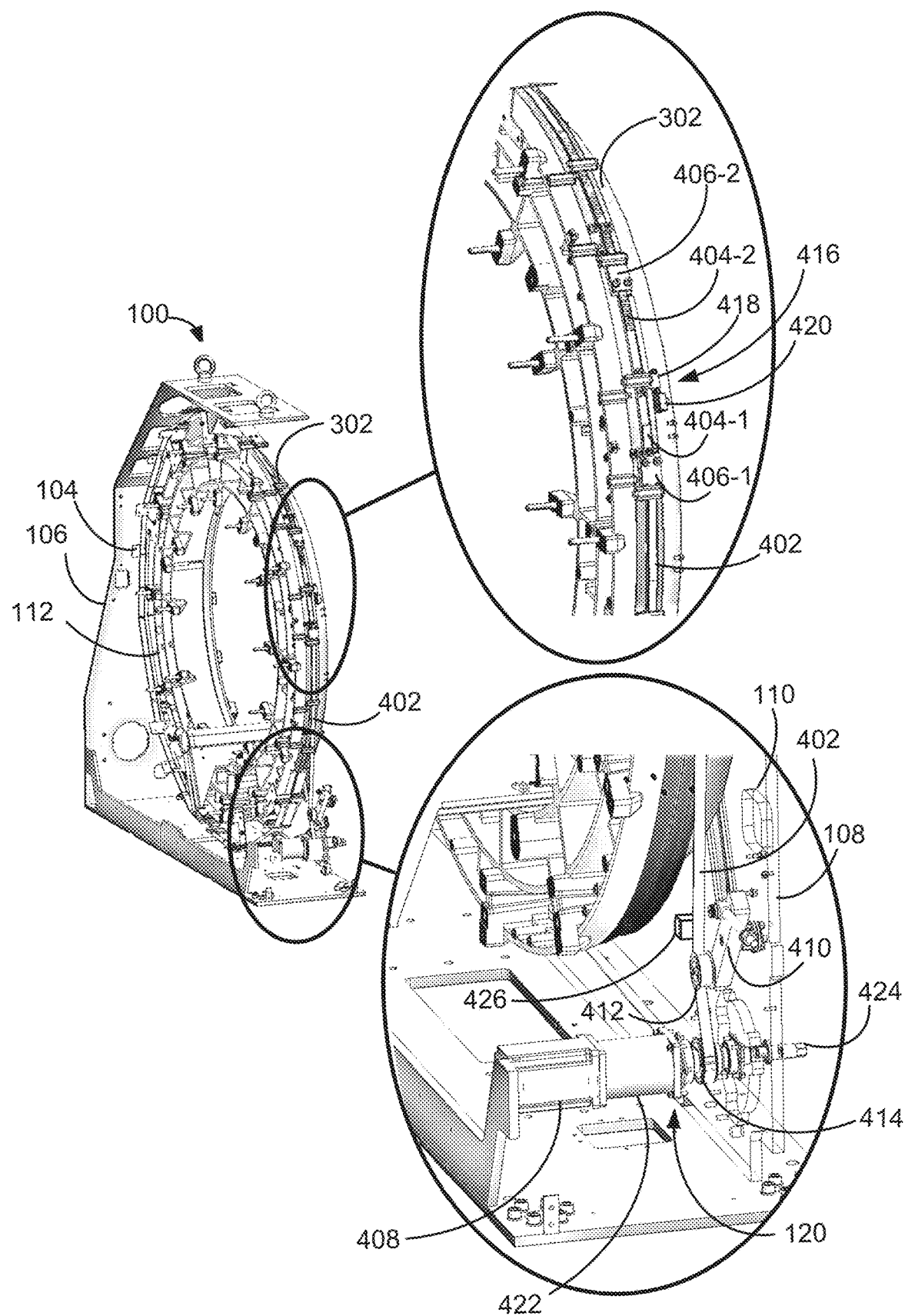
FIG. 4 is a perspective view simplified illustration of an N-M imaging system gantry in accordance with some embodiments of the invention.

In some embodiments and as shown in FIG. 4, which is a perspective view simplified illustration of a partial N-M imaging system gantry in accordance with some embodiments of the invention, driving belt 402 comprises an open flat belt having two ends 404-1 and 404-2. In the embodiment depicted in FIG. 4, N-M imaging system rotor 112 may not necessarily need to rotate a full 360 degree circumferential rotation allowing for a belt 402 having a length shorter than the circumference of outer circumferential surface 302. Additionally and optionally, driving belt 402 does not necessarily comprise a closed ring.

A first potential advantage of this configuration is in that the length of driving belt 402 is shorter than the circumference of rotor 112 outer circumferential surface 302 on which it is disposed thus reducing cost of driving belt 402. A second potential advantage of this configuration is in that driving belt 402 can be removed and/or replaced by threading the belt onto outer circumferential surfaces 302 negating a need to remove and return gantry components from and onto rotor 112 that may interfere with mounting a ring-form driving belt 112 onto outer circumferential surfaces 302. This results in a faster and simpler belt replacement operation and overall N-M imaging system maintenance.

As shown in the exemplary embodiment depicted in FIG. 4, ends 404-1/404-2 are each coupled to respective clamps 406-1/406-2. In some embodiments, clamps 406-1/406-2 are fixedly attached to outer circumferential surface 302 of rotor 112. Replacement of driving belt 402 is executed by opening clamps 406-1/406-2, releasing ends 404-1/404-2 from their respective clamps and pulling on one end 404-1/404-2 to unthread driving belt 402. A new belt 402 can then be threaded along outer circumferential surface 302 and ends 404-1/404-2 reattached to their respective clamps 406-1/406-2.

In the exemplary embodiment depicted in FIG. 4, driving belt 402 is driven by rotor driving assembly 120 including at least one motor 408, one or more driving belts 402 and a tensioning system 450. Tensioning system 450 comprises at least one tensioning arm 410 and a pulley 412. In some embodiments, both motor and tensioning system 450 are controlled by controller 101. In some embodiments, rotor driving assembly 120 comprises one or more motors 408 and one or more gearboxes 422 that deliver power via an output axis 424. In some embodiments, during the belt 402 replacement process as described elsewhere herein, driving belt 402 is threaded onto a pivotable tensioning arm 410 pulley 412 and rotor driving assembly 120 pulley 414 mounted on output axis 424. In some embodiments, pulley 412 is an idle pulley. In some embodiments, as described elsewhere herein, driving belt 402 is flat and is placed around a circumferentially flat portion of rotor 112 outer circumferential surface 302. The ability of driving belt 402 to drive and bring rotor 112 to rotate depends on friction between flat surfaces of driving belt 402 and outer circumferential surface 302 in contact with each other. The force of friction should be sufficient to prevent sliding of driving belt 402 over flat outer circumferential surface 302, while, concurrently applying tension forces to driving belt 402 within allowable limits that will not bring driving belt 402 to tear. In some embodiments, the level of friction and/or tension are controlled by controller 101 via tensioning arm 410.

A potential advantage of adjustable tension of driving belt 402 is in that friction of driving belt 402 over rotor 112 can be adjusted and lessened for safety purposes.

Tensioning arm 410 is pivotly adjustable manually and/or automatically by controller 101. The degree of tension affects the accuracy of rotation of rotor 112 and requires calibration via tensioning arm 410. In some embodiments and optionally, gantry 100 comprises a driving belt tension sensor 426 in communication with controller 101 that provides controller 101 with feedback information regarding the level of tension in driving belt 402. In some embodiments, tension sensor 412 comprises an ultrasound sensor but may comprise any other compatible tension sensor.

Figure 5:
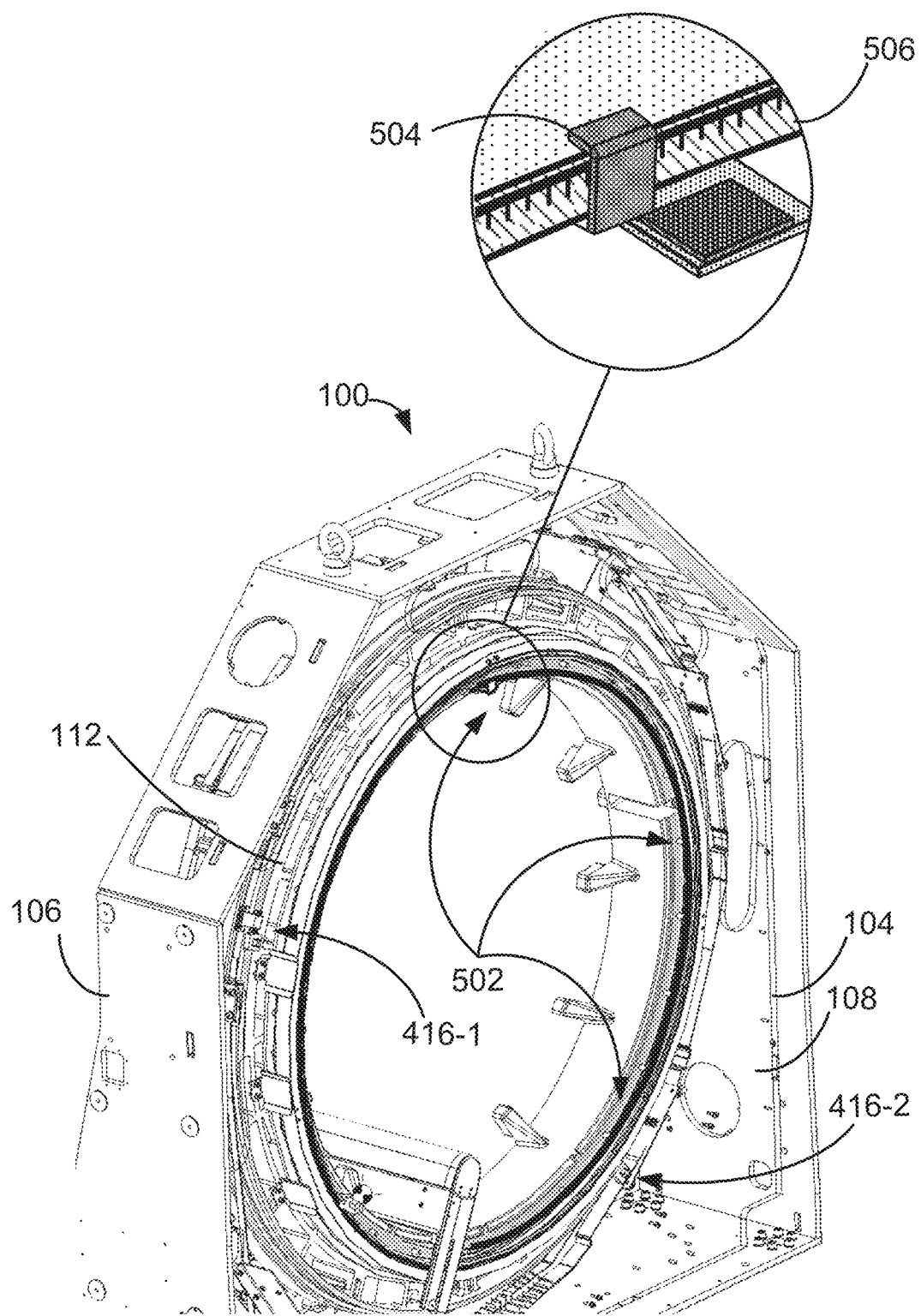
FIG. 5 is a perspective view simplified illustration of an N-M imaging system gantry in accordance with some embodiments of the invention.

As illustrated in the exemplary embodiment shown in FIGS. 4 and 5, gantry rotor 112 comprises one or more stoppers 416. In some embodiments, stoppers 416 comprise mechanical stoppers. In some embodiments, stopper 416 comprises a first lever and a second lever so that one of the levers unidirectionally interferes with a path of travel of the other lever as rotor 112 rotates in a first direction and allow rotor 112 to rotate in an opposite second direction. For example, in some embodiments, stopper 416 comprises a first lever 418 mounted on rotor 112 and a second lever 420 positioned on stator 104. In some embodiments and as showed in an embodiment depicted in FIG. 5, gantry rotor 112 comprises a first rotation direction stopper 416-1 and a second rotation direction stopper 416-2. Stoppers 416 block rotation of rotor 112 when respective clamps 406-1/406-2 approach rotor driving assembly 120.

Exemplary Rotor Movement Linear Encoder

In some embodiments, and as shown in FIG. 5, which is a perspective view simplified illustration of an N-M imaging system gantry in accordance with some embodiments of the invention, N-M imaging system optionally includes a rotor rotation linear encoder 502 comprising one or more sensors 504 and one or more scale strips 506. Rotor rotation linear encoder 502 is in communication with controller 101 and is configured to provide controller 101 with feedback regarding the degree of rotation of rotor 112 in respect to stator 104 at any point along rotor 112 path of rotation. Optionally linear encoder 502 comprises a magnetic scale strip.

Alternatively and optionally, N-M imaging system comprises an optical encoder and scale strip. In some embodiments, sensor 504 comprises a sensor flag. In some embodiments, sensor 504 is coupled to stator 104 in a stationary position and scale 506 moves across sensor 504 as rotor 112 rotates. In some embodiments and optionally, scale 506 is disposed along a circumferential surface of rotor 112, e.g., centrally facing inner surface 304 or any circular surface concentric with a circumferential surface of rotor 112. Linear encoder sensor 502 provides controller 101 with feedback information regarding spatial position of gantry 100 rotor 112, for example, degree of circumferential rotation of rotor 112 in respect to a given point, e.g., stator 104.

A potential advantage in use of a linear encoding system is in that controller 101 is provided with units of movement of rotor 112 read by encoder sensor 504 directly off scale 506 negating the need to calculate a conversion ratio as done at times in other encoding systems. A potential advantage in the location of linear encoder is in that the encoder is positioned after the output axis of the driving system, e.g., motor, transmission and driving belt tensor. This configuration provides a true accurate reading of movement of the load (e.g., rotor 112) being driven and does not need to be corrected for tolerances in the driving system. For this reason, all encoders in the exemplary embodiments depicted elsewhere herein are positioned on or after the output axis of the respective driving systems.

Exemplary Detection unit extendable arm driving system

Reference is now made to FIGS. 6A, 6B, 6C and 6D, collectively referred to as FIGS. 6A-D, which are side view simplified illustration of arrangement of an N-M imaging system detection units in an N-M imaging system gantry and a perspective view simplified illustration of a detection unit head and extendable arm in accordance with some embodiments of the invention.

FIG. 6A illustrates an exemplary embodiment of an N-M imaging system gantry 100 comprising twelve-detection units 602, all of which are in a "Home" or retracted position as shown in FIG. 6C. FIG. 6B illustrates the exemplary embodiment of the N-M imaging system gantry 100 depicted in FIG. 6A in which the twelve detection units 602 are all in a fully (maximal) extended position as shown in FIG. 6D.

Figure 12:
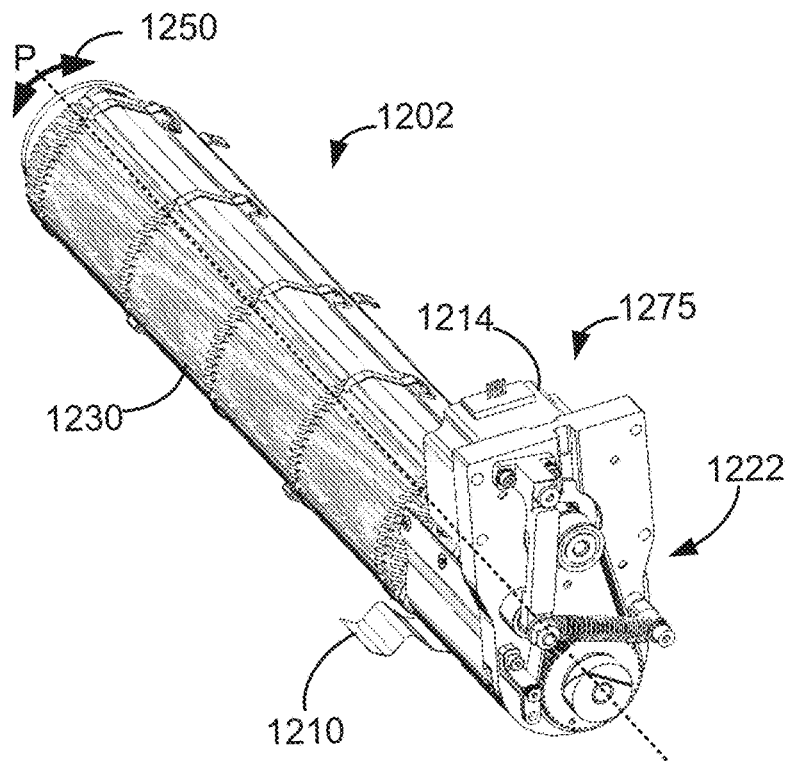
FIG. 12 is a perspective view simplified illustration of an N-M imaging system detection unit and driver assembly in accordance with some embodiments of the invention.

As shown in FIGS. 6C and 6D, detection unit 602 comprises an extendable arm 604 and a scanning unit 118 comprising one or more scanning columns 1202 housing Multi-Pixel Photon Counters (MPCs) (FIG. 12, 1204). In some embodiments and as is explained in greater detail elsewhere herein, extendable arm 604 comprises a linear drive system 608 that extends arm 604 carrying scanning unit 118 radially inward towards a center of rotation of gantry 100 and retracts arm 604 carrying scanning unit 118 in an opposite direction radially outwards. The Linear drive system 608 of arm 604 is in bidirectional communication with controller 101 as explained elsewhere herein.

As shown in the exemplary embodiment illustrated in FIGS. 6C and 6D, detection unit 602 comprises a stationary chassis 606 and an extendable arm 604, axially moveable and extendable from and along chassis 606. In some embodiments, chassis 606 comprises a coupling 625 sized to couple to detection unit couplings 116 onto rotor 112 and one or more linear driving systems 608 that drives extendable arm 604 and Scanning unit 118 axially along stationary chassis 606 from a "Home" retracted position to a fully extended position and vice versa in direction indicated by arrow 650 as described elsewhere herein. In some embodiments, linear drive system 608 is configured to bidirectionally move extendable arm 604 and a scanning unit 118 in a stepwise fashion and is configured to stop at any point in accordance with input from controller 101.

Additionally and optionally, detection unit 602 comprises a counter weight 610 that balances the weight of extendable arm 604 and scanning unit 118 and thereby enables the use of low power driving motor 614. Each extension/retraction of extendable arm 604 brings concurrent movement of counter weight 610 in an opposite direction as indicated by double headed arrow designated reference numeral 652.

Reference is now made to FIG. 7, which is a perspective exploded view simplified illustration of an N-M imaging system detection unit linear drive system 608 in accordance with some embodiments of the invention. As shown in the exemplary embodiment shown in FIG. 7, linear drive system 608 is configured to axially extend and retract extendable arm 604 and comprises a motor 614 having an output axis 702 coupled to a driver pulley 704. In some embodiments, motor 614 rotates belt 706 driver pulley 704 in a clockwise or counter clockwise in a continuous or stepped motion as indicated by a double-headed arrow 750. In some embodiments, pulley 704 comprises a ribbed surface 710, which corresponds to a ribbed inner surface 708 of belt 706. In some embodiments, belt 706 comprises a looped belt mounted on driving pulley 704 and an idler pulley 712.

In some embodiments and as shown in FIG. 8, which is a perspective view simplified illustration of a detection unit linear drive system in accordance with some embodiments of the invention, a belt 806 comprises a smooth inner flat surface 808 mounted on a driver pulley 804 and an idler pulley 812 having smooth belt contacting surfaces 814.

Referring back to FIG. 7, in some embodiments, belt 706 comprises one or more couplings 730 for attaching extendable arm 604 (not shown) and one or more couplings 732 to couple a counter weight 610 (not shown) carrier 736 respectively to belt 706. Couplings 730 and 732 are positioned on opposite sides of belt 706 positioning extendable arm 604 carrying scanning unit 118 and counter weight 610 on opposite sides of belt 706. In some embodiments and as shown in FIGS. 6C and 6D, a longitudinal axis of a wide aspect of counter weight 610 parallels a longitudinal axis of scanning unit 118. In some embodiments, extendable arm 604 is coupled to a first portion 724 of belt 706 between pulleys 704/712 moving in a first direction, via a coupling 730 on inner surface 708 or outer surface 728 of belt 706. In some embodiments, counter weight 610 is coupled to a second portion 734 of belt 706 between pulleys 704/712 moving in a second opposite direction, via a coupling 732 on inner surface 708 or outer surface 728 of belt 706 between pulleys 704/712. In this configuration, when belt 706 moves for a distance (d), extendable arm 604 is driven in a first direction along the same distance (d) while counter weight 610 is concurrently driven at the same speed as extendable arm 604 but in an opposite second direction along the same distance (d). Being attached to belt 706 both extendable arm 604 and counter weight 610 move in opposite directions in reference to each other and to chassis 606 at the same speed and for the same distance. A potential advantage of this configuration is in that counter weight 610 balances the weight of extendable arm 604 enabling the use of a low power motor 614.

In some embodiments, one or both pulleys 704/712 are coupled to chassis 606 by adjustable couplings that allow adjusting the distance between pulleys 704/712 thereby adjusting tension of belt 706 mounted on pulleys 704/712. In some embodiments and optionally, chassis 606 comprises a belt 706 tension sensor 720 in communication with controller 101 that provides controller 101 with feedback information regarding the level of tension in driving belt 706. In some embodiments, tension sensor 720 comprises an ultrasound sensor but may comprise any other compatible tension sensor. Alternatively and optionally, in some embodiments linear drive system 608 comprises a tensioning arm system (not shown) as explained elsewhere herein.

In some embodiments, e.g. the exemplary embodiment shown in FIG. 9, which is a perspective exploded view simplified illustration of a detection unit linear drive system 608 in accordance with some embodiments of the invention, linear drive system 608 driving belt 906 comprises an open flat belt having two ends 904-1 and 904-2. In the embodiment depicted in FIG. 9 driving belt 906 may not necessarily need to rotate a full 360 degree circumferential rotation allowing for a belt 906 to have a length shorter than a full circumference of a looped belt as described elsewhere herein. Additionally and optionally, driving belt 906 does not necessarily comprise a closed ring.

A first potential advantage of this configuration is in that the length of driving belt 906 is shorter than a circumference of looped belt. A second potential advantage of this configuration is in that driving belt 906 can be removed and/or replaced by threading the belt around pulleys 704/712 negating a need to remove and return chassis 606 or extendable arm 604 components that may interfere with mounting a ring-form (looped) driving belt 112 onto pulleys 704/712. This results in a faster and simpler belt replacement operation and overall N-M imaging system maintenance.

As shown in the exemplary embodiment depicted in FIG. 9, ends 904-1/904-2 are each coupled to respective clamps 902-1/902-2. In some embodiments, clamps 406-1/406-2 are movably attached to chassis 606 and in some embodiments, to counter weight 610. Replacement of driving belt 906 is executed by opening clamps 902-1/902-2, releasing ends 904-1/904-2 from their respective clamps and pulling on one end 904-1/904-2 to unthread driving belt 906. A new belt 906 can then be threaded onto pulleys 704/712 and ends 904-1/904-2 reattached to their respective clamps 902-1/902-2.

Exemplary Extendable Arm Movement Linear Encoder

Figure 10:
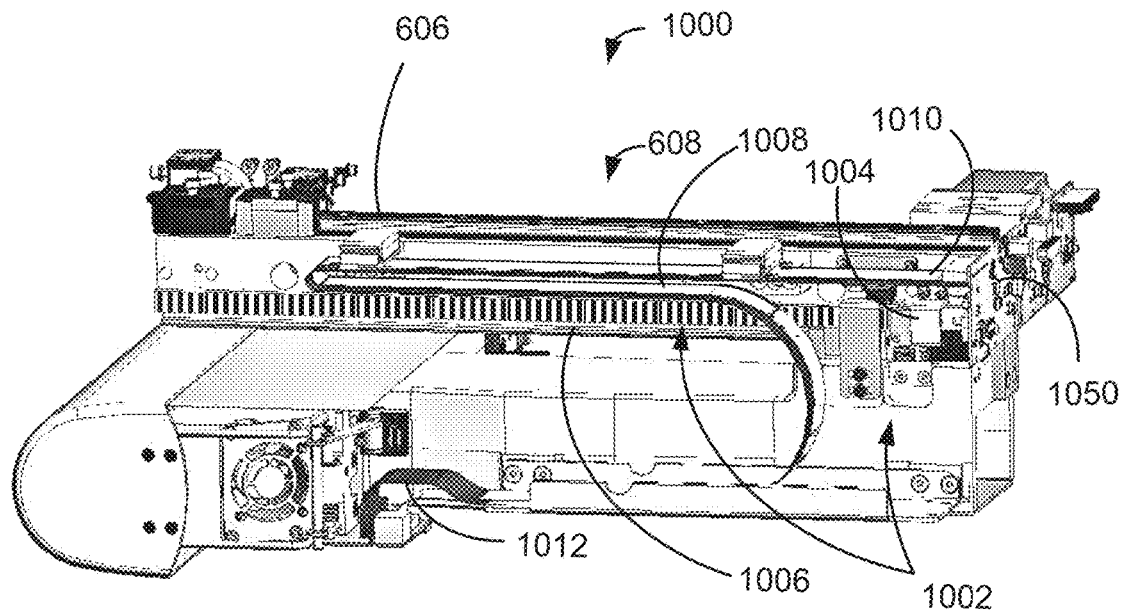
FIG. 10 is a perspective view simplified illustration of an N-M imaging system detection unit in a "Home" or retracted position in accordance with some embodiments of the invention.

Referring now to FIG. 10, which is a perspective view simplified illustration of an N-M imaging system detection unit 1000 in a "Home" or retracted position in accordance with some embodiments of the invention viewed from a direction indicated in FIG. 7 by an arrow designated reference number 760. In some embodiments, and as shown in FIG. 10, detection unit 1000 linear drive system 608 optionally includes a linear encoder 1002 comprising a sensor 1004 and a scale strip 1006. Optionally linear encoder 1002 comprises a magnetic scale strip. Alternatively and optionally, detection unit 1000 comprises an optical encoder and scale strip. In some embodiments, sensor 1004 comprises a sensor flag. In some embodiments, sensor 1004 is coupled to a stationary portion of detection unit 1000 e.g., chassis 606, which remains in a stationary position in respect to extendable arm 604, being coupled to detection unit couplings 116 of rotor 112. Scale 1006 is coupled to extendable arm 604 and moves across sensor 1004 as extendable arm 604 is extended or retracted. In some embodiments alternatively and optionally, scale 1006 is disposed along chassis 606 and sensor 1004 is coupled to and moves with extendable arm 604 as it extends or retracts along linear scale 1006. Linear encoder sensor 1002 provides controller 101 with information regarding spatial position of extendable arm 604, for example, degree of radial inwards extension in respect to gantry 100 rotor 112 or other extendable arms.

A potential advantage in use of a linear encoding system is in that controller 101 is provided with units of movement of extendable arm 604 read by encoder sensor 1004 directly off scale 1006 negating the need to calculate a conversion ratio as done at times in other encoding systems. A potential advantage in the location of linear encoder is in that the encoder is positioned after output axis 702 of the extendable arm 604 driving system, e.g., motor 614 and driving belt 706 tensor, when exists. This configuration provides a true accurate reading of movement of the load (e.g., extendable arm 604) being driven and does not need to be corrected for tolerances in the driving system.

Exemplary Flat Cable

Referring still to the exemplary embodiment shown in FIG. 10, detection units 602 comprise flat (ribbon) data and power cables 1008 that transfer data and power between system components (e.g., chassis 606 and extendable arm 604). In some embodiments, flat cable 1008 comprises a double-layered flat cable carrying both power and data. In some embodiments, flat cables comprise a plurality of conducting wires running parallel to each other on the same flat plane. As a result, the cable is wide and flat. A potential advantage in using a flat cable is in that a single flat cable may transfer many types of data and thus reduce the number of cables and/or wires required to support each function on the N-M imaging system.

Figure 11A:
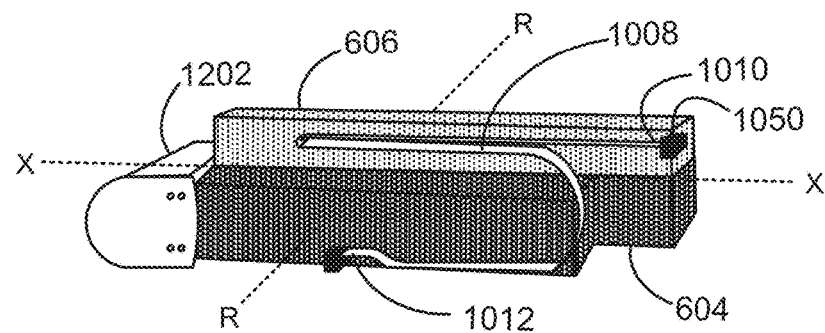
FIGS. 11A and 11B are perspective view simplified illustrations of a detection unit in retracted and extended configurations in accordance with some embodiments of the invention.
Figure 11B:
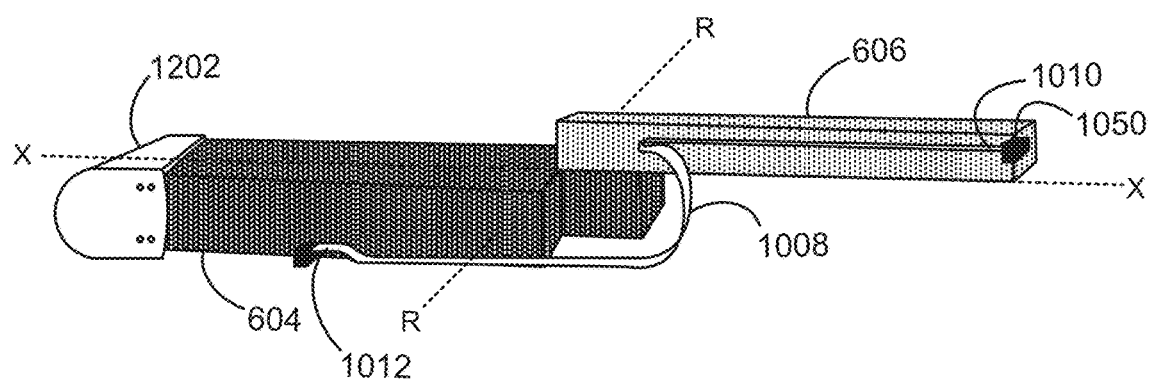

As shown in FIG. 10, flat cable 1008 comprises one end 1010 attached to a data information cable connector 1050 on chassis 606 and a second end 1012 attached to Scanning unit 118 mounted on extendable arm 604. FIGS. 11A and 11B, which are perspective view simplified illustrations of detection unit 1000 in retracted and extended configurations in accordance with some embodiments of the invention.

In the exemplary embodiment depicted in FIGS. 11A and 11B movement of a flat cable 1008 is shown in response to movement of extendable arm 604 from a "Home" or retracted position (FIG. 11A) to a fully extended position (FIG. 11B). As shown in the exemplary embodiments shown in FIGS. 11A and 11B, flat cable 1008 flexes with a rolling-flex axial movement along axis of movement (X) of extendable arm 604 with little or no lateral movement along axis (R) perpendicular to axis (X).

A potential advantage in using a flat cable is in that flat cables support rolling-flex movement and resist torsion or twisting. Hence, flat cables maintain movement in a single dimension (e.g., axial movement, parallel to movement of extendable arm 604 in respect to chassis 606) negate the need for a cable retractor and thus occupy less space reducing the bulkiness of detection unit 1000. This characteristic also allows to leave excess cable if necessary, the excess remaining along the same single dimension.

A potential advantage in using a flat cable is in that flat cables reciprocating movement along the single-dimension over long periods of time without breakage and are therefore suitable for connecting between parts that move axially in a reciprocating motion in respect to each other e.g., chassis 606 and extendable arm 604.

A potential advantage in using a flat cable is in that the characteristic reciprocating motion along a single dimension of flat cables enables connecting power and/or data conduits between stationary, moving or even rotating parts negating the need for slip ring/s and/or brushes used in conventional wiring solutions.

A potential advantage in using a flat cable is in that flat cables reciprocating movement along the single-dimension negating the need for retractors between moving parts.

Exemplary Detection Unit Moving Scanning Column (MPC)

Reference is now made to FIG. 12, which is a perspective view simplified illustration of an N-M imaging system detection unit and driver assembly in accordance with some embodiments of the invention. N-M imaging system gantry 100 rotor 112 carries one or more scanning columns 1202. In some embodiments, one or more scanning columns 1202 comprise Multi-Pixel Photon Counters (MPCs) 1230. In some embodiments, scanning columns 1202 pivot bidirectionally at least partially along a circular path of less than 360 degrees, or less than 300 degrees, or less than 270 degrees, or less than 210 degrees, or less than 150 degrees, or any intermediate angle around a pivot axis (P) parallel to the longitudinal axis of scanning columns 1202 as indicated by an arrow 1250.

In some embodiments, scanning columns 1202 is driven by a driver assembly 1275 comprising at least one dedicated motor 1214 positioned peripherally to scanning columns 1202. In some embodiments, motor 1214 generates a stepped rotational mechanical driving force effected on scanning columns 1202 via a gearbox 1222 and output axis 1206. Output axis 1206 terminates at a coupling 1208 that couples scanning columns 1202 to driving assembly 1204.

In some embodiments, one or more scanning columns 1202 are in data and power communication with controller 101 and electrical power source 109 via a flat cable 1210 in communication with flat cable 1008 of chassis 606 and extendable arm 604.

Exemplary Rotating Encoder

Figure 13:
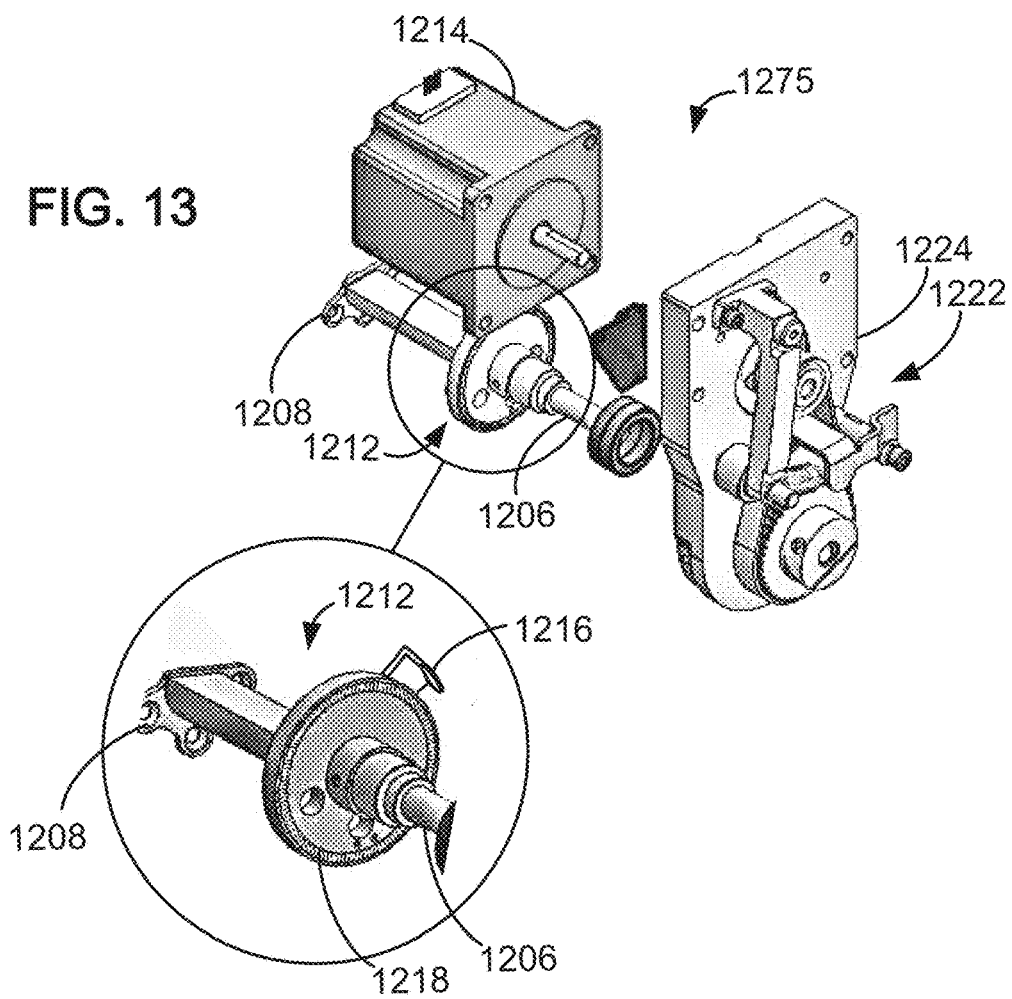
FIG. 13 is a perspective view simplified illustration of an N-M imaging system detection unit rotation driver assembly in accordance with some embodiments of the invention.

Referring now to FIG. 13, which is a perspective view simplified illustration of an N-M imaging system scanning columns 1202 rotation driver assembly 1204 in accordance with some embodiments of the invention. In some embodiments, and as shown in FIG. 13, scanning columns 1202 rotation driver assembly 1275 optionally includes a rotary encoder 1212 comprising a sensor 1216 and a scale disc 1218. Optionally rotary encoder 1212 comprises a magnetic scale strip. Alternatively and optionally, scanning columns 1202 comprises an optical rotary encoder and scale strip. In some embodiments, sensor 1216 comprises a sensor flag. In some embodiments, sensor 1216 is coupled to scanning columns 1202 driver assembly 1275 chassis 1224 which remains in a stationary position in respect to scanning columns 1202. In some embodiments, scale disc 1218 is coupled to output axis 1206 proximally to coupling 1208 and moves across sensor 1216 as scanning columns 1202 pivots back and forth. In some embodiments and optionally, rotary scale strip 1218 is disposed circumferentially about scanning columns 1202 driver assembly chassis and sensor 1216 is coupled to and moves with scanning columns 1202 as it pivots about rotary encoder scale strip 1218. Rotary encoder 1212 provides controller 101 with information regarding spatial position of scanning columns 1202, for example, degree of pivot in respect to gantry 100 or a vector of gravity.

A potential advantage in use of a rotary encoding system is in that controller 101 is provided with units of rotation/pivot of scanning columns 1202 read by encoder sensor 1216 directly off scale disc 1218 negating the need to calculate a conversion ratio as done at times in other encoding systems. A potential advantage in the location of rotary encoder 1212 is in that the encoder is positioned on or after output axis 1206 of the driver assembly 1204, e.g., motor 1214 and gearbox 1222. This configuration provides a true accurate reading of movement of the load (e.g., scanning columns 1202) being driven and does not need to be corrected for tolerances in the driving system.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A Nuclear Medicine (N-M) imaging system gantry comprising:

at least one stationary stator;

at least one rotor rotatably mounted on said stator and including at least one detection unit having at least one Multi-Pixel Photon Counter (MPC); and at least one rotor driving assembly comprising:
  at least one motor; and
  a flat driving belt mounted on a peripheral flat surface of said rotor and driven by said motor;

wherein said belt is an open belt having two ends, and wherein each of said belt ends is coupled to a respective clamp fixedly attached to a circumference of said rotor.

2. The gantry according to claim 1, wherein said rotor driving assembly motor comprises an output axis and a pulley mounted on said output axis.

3. The gantry according to claim 1, wherein a length of said belt is equal to or shorter than a circumference of said rotor.

4. The gantry according to claim 1, wherein said rotor driving assembly comprises at least one driving belt tensioning system.

5. The gantry according to claim 4, wherein said driving belt tensioning system comprises at least one pivotable tensioning arm and a pulley.

6. The gantry according to claim 4, wherein said N-M imaging system comprises at least one controller in communication with at least said rotor driving assembly and a level of friction between said belt and said peripheral flat surface is controlled by said controller.

7. The gantry according to claim 6, wherein said controller controls said level of friction between said belt and said peripheral flat surface by controlling degree of pivot of said tensioning arm.

8. The gantry according to claim 6,
  wherein said at least one driving belt tensioning system comprises a driving belt tension sensor; and
  wherein said driving belt tension sensor is in communication with said controller and provides said controller with feedback information regarding the level of tension in said driving belt.

9. The gantry according to claim 6, wherein said gantry comprises a rotor rotation linear encoder.

10. The gantry according to claim 9, wherein said linear encoder is in communication with said controller and provides said controller with feedback information regarding spatial position of said rotor at any point along said rotor path of rotor rotation.

11. The gantry according to claim 9, wherein said encoder comprises at least one sensor and at least one scale strip; and
  wherein said encoder is coupled to said stator and said scale strip moves across said sensor as said rotor rotates.

12. The gantry according to claim 4, wherein said tensioning system comprises a driving belt tension sensor.

13. The gantry according to claim 12, wherein said sensor comprises an ultrasound sensor.

14. The gantry according to claim 1, wherein said rotor comprises one or more stoppers.

15. The gantry according to claim 14, wherein said stoppers comprise a mechanical stopper having a first lever mounted on said rotor and a second lever positioned on said stator.

16. The gantry according to claim 15, wherein one of said levers unidirectionally interferes with a path of travel of the other lever as said rotor rotates in a first direction and allows said rotor to rotate in an opposite second direction.

17. The gantry according to claim 14, wherein said rotor comprises a first rotation direction stopper and a second rotation direction stopper.

18. The gantry according to claim 1,
  wherein each of said belt ends is coupled to a respective clamp fixedly attached to a circumference of said rotor; and
  wherein said rotor comprises one or more stoppers, wherein said stoppers block rotation of said rotor when at least one of said clamps approaches said rotor driving assembly.

19. A Nuclear Medicine (N-M) imaging system gantry comprising:
  at least one stationary stator;
  at least one rotor rotatably mounted on said stator and including at least one detection unit having at least one Multi-Pixel Photon Counter (MPC); and
  at least one rotor driving assembly comprising:
    at least one motor; and
    a flat driving belt mounted on a peripheral flat surface of said rotor and driven by said motor;
  wherein said rotor driving assembly comprises at least one driving belt tensioning system; and
  wherein said N-M imaging system comprises at least one controller in communication with at least said rotor driving assembly and a level of friction between said belt and said peripheral flat surface is controlled by said controller.

20. The gantry according to claim 19, wherein said driving belt tensioning system comprises at least one pivotable tensioning arm and a pulley.

21. The gantry according to claim 19, wherein said controller controls said level of friction between said belt and said peripheral flat surface by controlling degree of pivot of said tensioning arm.

22. The gantry according to claim 19, wherein said tensioning system comprises a driving belt tension sensor.

23. The gantry according to claim 19,
  wherein said at least one driving belt tensioning system comprises a driving belt tension sensor; and
  wherein said driving belt tension sensor is in communication with said controller and provides said controller with feedback information regarding the level of tension in said driving belt.

24. A Nuclear Medicine (N-M) imaging system gantry comprising:
  at least one stationary stator;
  at least one rotor rotatably mounted on said stator and including at least one detection unit having at least one Multi-Pixel Photon Counter (MPC); and
  at least one rotor driving assembly comprising:
    at least one motor; and
    a flat driving belt mounted on a peripheral flat surface of said rotor and driven by said motor;
  wherein said rotor comprises one or more stoppers; and
  wherein said stoppers comprise a mechanical stopper having a first lever mounted on said rotor and a second lever positioned on said stator.

25. The gantry according to claim 24, wherein one of said levers unidirectionally interferes with a path of travel of the other lever as said rotor rotates in a first direction and allows said rotor to rotate in an opposite second direction.

26. The gantry according to claim 24, wherein said rotor comprises a first rotation direction stopper and a second rotation direction stopper.

* * * * *